United States Patent [19]

König et al.

[11] Patent Number: 4,597,910

[45] Date of Patent: Jul. 1, 1986

[54] BIS-(4-ISOCYANATOPHENOXY)-ALKANES AND A PROCESS FOR THE PRODUCTION THEREOF

[75] Inventors: Klaus König, Leverkusen; Peter Heitkämper, Dormagen, both of Fed. Rep. of Germany

[73] Assignee: Bayer Aktiengesellschaft, Leverkusen, Fed. Rep. of Germany

[21] Appl. No.: 796,128

[22] Filed: Nov. 8, 1985

[30] Foreign Application Priority Data

Nov. 23, 1984 [DE] Fed. Rep. of Germany ....... 3442689
Jul. 18, 1985 [DE] Fed. Rep. of Germany ....... 3525606

[51] Int. Cl.⁴ .................... C07C 118/00; C08G 18/00
[52] U.S. Cl. .................................. 560/359; 521/170; 528/48
[58] Field of Search ................. 260/453 AM, 453 AR

[56] References Cited

U.S. PATENT DOCUMENTS 4,421,870 12/1983 Stutz et al. ......................... 521/160
4,448,946 5/1984 Stutz et al. ......................... 528/67

OTHER PUBLICATIONS

Becker, Braun, Kunststoff-Handbuch, vol. 7, 2nd Edition, 1983, Carl Hanser Verlag, pp. 391 et seq.

Primary Examiner—A. Siegel
Attorney, Agent, or Firm—Gene Harsh; Joseph C. Gil; Lyndanne M. Whalen

[57] ABSTRACT

Bis-(4-isocyanatophenoxy)-alkanes corresponding to the formula

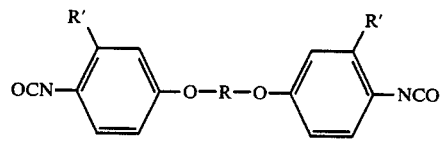

in which
R represents a divalent, saturated aliphatic hydrocarbon radical having from 2 to 6 carbon atoms with at least two carbon atoms between the two ether oxygen atoms, and
R' represents hydrogen or a methyl group with R' being the same on both rings, are produced by phosgenating the corresponding diamine or an adduct of the corresponding diamine. These diisocyanates are particularly useful in the production of isocyanate addition products having outstanding physical and mechanical properties.

8 Claims, No Drawings

BIS-(4-ISOCYANATOPHENOXY)-ALKANES AND A PROCESS FOR THE PRODUCTION THEREOF

BACKGROUND OF THE INVENTION

This invention relates to bis-(4-isocyanatophenoxy)-alkanes, bis-(4-isocyanato-3-methyl-phenoxy)alkanes and to a process for the production thereof.

The properties of polyurethane plastics, in particular of polyurethane elastomers, are essentially dependent upon the nature of the polyisocyanate used in their production. Aromatic diisocyanates, such as 4,4'-diisocyanato-diphenylmethane, tolylene diisocyanate and 1,5-diisocyanatonaphthalene are typically used in the production of polyurethane elastomers (see, e.g., Becker, Braun, Kunststoff-Handbuch, Vol. 7, 2nd Edition (1983), Carl Hanser Verlag, pages 391 et seq).

Although 4,4'-diisocyanato-diphenylmethane and tolylene diisocyanate produce elastomers inexpensively, the elastomers obtained often have unsatisfactory mechanical and thermal properties. High-grade polyurethane elastomers may, for example, be obtained if 1,5-diisocyanatonaphthalene is used as the diisocyanate component. Cast elastomers based on this diisocyanate are distinguished by excellent mechanical properties.

However, 1,5-diisocyanatonaphthalene suffers from the disadvantage that the crude material used for the production thereof, naphthalene, is available only in limited quantities. Furthermore, the nitration of naphthalene inevitably leads to an isomer mixture of nitronaphthalenes from which 1,5-dinitronaphthalene must be isolated. The purification by distillation of 1,5-diisocyanatonaphthalene obtained from the dinitro compound (by hydrogenation and subsequent phosgenation of the resulting diamine) is difficult because 1,5-diisocyanatonaphthalene tends to sublimate. This means that 1,5-diisocyanatonaphthalene is expensive.

The processing of 1,5-diisocyanatonaphthalene is often difficult because its melting point and vapor pressure are relatively high. These properties often do not permit 1,5-diisocyanatonaphthalene to be reacted directly as melt. Technically costly processing methods and protective measures are then required to prevent chemical and operational problems.

Many attempts have been made to find a comparable alternative to 1,5-diisocyanatonaphthalene as a diisocyanate component in the production of high-grade polyurethane plastics. For example, German Offenlegungsschriften Nos. 3,138,421 and 3,138,422 describe the production of polyurethane elastomers using 4,4'-diisocyanato-(1,2)-diphenylethane as the diisocyanate component. Admittedly, plastics with good mechanical properties can be obtained with this diisocyanate, but the production of 4,4'-diisocyanato-diphenyl-ethane-(1,2) is very involved and costly and hitherto difficult to realize commercially.

Many attempts have been made to use the comparatively inexpensive 4,4'-diisocyanato-diphenylmethane instead of 1,5-diisocyanatonaphthalene for the production of high-grade polyurethane elastomers. However, all of these attempts have failed to produce polyurethane elastomers based on this diisocyanate which have mechanical and thermal properties corresponding to 1,5-diisocyanatonaphthalene-based polyurethane elastomers.

SUMMARY OF THE INVENTION

It is an object of the present invention to provide new diisocyanates.

It is also an object of the present invention to provide new diisocyanates which will produce high-grade polyurethane elastomers having properties comparable to polyurethanes produced from 1,5-diisocyanatonaphthalene.

It is another object of the present invention to provide a process for the production of these new diisocyanates which process is both economic and relatively simple.

It is a further object of the present invention to provide isocyanate addition products having outstanding physical properties and a process for their production.

These and other objects which will be apparent to those skilled in the art are accomplished by phosgenating a bis-(4-amino-phenoxy)-alkane corresponding to a specified formula or its hydrogen chloride or carbon dioxide adduct to form a bis-(4-isocyanato-phenoxy)-alkane corresponding to a specified formula. The thus-obtained isocyanate may then be reacted with a compound containing isocyanate-reactive hydrogen atoms to form an isocyanate addition product having outstanding physical properties.

DETAILED DESCRIPTION OF THE INVENTION

The present invention relates to bis-(4-isocyanatophenoxy)-alkanes corresponding to the general formula

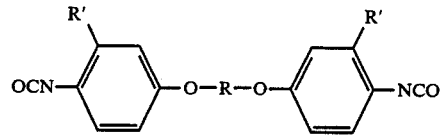

in which

R represents a divalent, saturated aliphatic hydrocarbon radical having from 2 to 6 carbon atoms with at least 2 carbon atoms between the two ether oxygen atoms; and R' represents hydrogen or a methyl group, provided that R' is the same on both rings.

The present invention also relates to a process for the production of bis-(4-isocyanatophenoxy)-alkanes corresponding to the above formula in which bis-(4-amino-phenoxy)-alkanes corresponding to the general formula

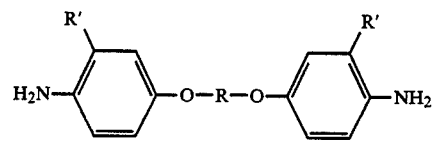

in which R and R' are as defined above, or the adducts thereof with hydrogen choride or carbon dioxide, are reacted in a known manner with phosgene.

The present invention also relates to the use of bis-(4-isocyanatophenoxy)-alkanes corresponding to the above formula as structural components in the production of isocyanate addition products such as polyurethane plastics by the isocyanate polyaddition process.

Some of the diamines useful as starting materials in the process according to the invention are known and described in the literature. See, for example, Journal fur Praktische Chemie, Vol. 27 (1883), pages 206 and 207: Archiv der Pharmazie, Vol. 236, (1898), pages 260 to 262, and Ophthalmologica, Vol. 136 (1958), pages 332 to 344. Such diamines are conventionally produced from dinitro compounds by reduction with base metals (such as tin or iron), in the presence of acids or by catalytic hydrogenation. The diamines used in the process of the present invention may, of course, also be produced by any other known methods.

The dinitro compounds on which the diamine starting materials are based are easily obtainable. They can be produced, for example, by condensing alkali-4-nitrophenolate with alkanedihalides, or by reacting 4-nitrochlorobenzene with alkane diols in the presence of bases or by reacting 4-nitrochlorobenzene with (4-nitrophenoxy)-alkanols in the presence of bases. Other processes for the production of such dinitro compounds are described in the literature, for example in "The Chemistry of the Ether Linkage" (Publisher S. Patai, Interscience Publishers, 1967), pages 445 to 498.

Diamines corresponding to the general formula(e)

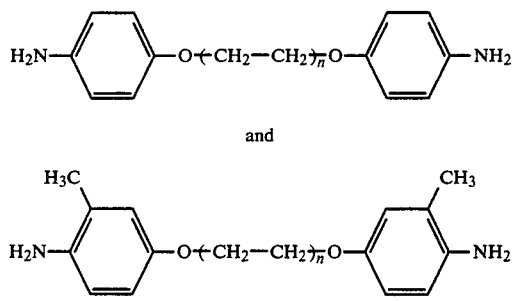

in which n represents 1,2, or 3 (most preferably 1), are preferably used in the process of the present invention. The preferred diisocyanates of the present invention are those obtained by using these preferred diamines. These preferred diisocyanates correspond to the general formula(e)

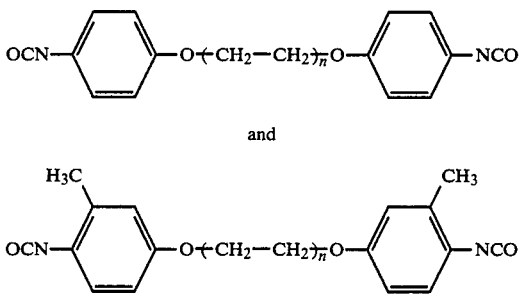

in which n represents 1,2 or 3 (most preferably 1).

The following are typical examples of starting amines which may be used in the process of the present invention: 1,2-bis-(4-aminophenoxy)-ethane; 1,4-bis-(4-aminophenoxy)-butane; 1,6-bis-(4-aminophenoxy)-hexane: 1,2-bis-(4-amino-3-methylphenoxy)-ethane, 1,4-bis-(4-amino-3-methylphenoxy)-butane or less preferably, 1,3-bis(-4-aminophenoxy)-propane, 1,5-bis-(4-aminophenoxy)-pentane, 1,2-bis(4-aminophenoxy)-propane and 1,3-bis-(4-aminophenoxy)-butane, 1,3-bis-(4-amino-3-methylphenoxy)-propane, 1,2-bis-(4-amino-3-methylphenoxy)-propane, 1,3-bis-(4-amino-3-methylphenoxy)-butane and 1,6-bis-(4-amino-3-methylphenoxy)-hexane. 1,2-bis-(4-aminophenoxy)-ethane and 1,2-bis-(4-amino-3-methylphenoxy)-ethane are the starting amines most preferably used in the process of the present invention. Correspondingly, 1,2-bis-(4-isocyanatophenoxy)-ethane and 1,2-bis-(4-isocyanato-3-methylphenoxy)-ethane are the most preferred isocyanates of the present invention.

The diamines to be phosgenated in accordance with the present invention may be used at commercial production purity or in purified form. They can be purified, for example, by dissolving them in dimethylformamide and then precipitating them with water or by distillation.

The diamines themselves can be phosgenated or they may be phosgenated in the form of their addition compounds with hydrogen chloride or with carbon dioxide. Phosgenation in accordance with the present invention may be carried out by known methods. Methods for phosgenating amines are described, for example, in Liebigs Annalen der Chemie, Vol. 562, Edition 1949, pages 75 to 109, in Ullmanns Encyclopädie der Technischen Chemie, Vol. 14, 4th Edition, 1977, pages 350 to 354 and in Houben-Weyl, Methoden der Organischen Chemie, Vol. E4, 4th Edition, 1983, pages 741 to 753.

The phosgenation may be carried out continuously or on a batch basis, preferably in the presence of an inert solvent. Examples of suitable solvents which are conventionally used for phosgenation include: aliphatic, cycloaliphatic or aromatic hydrocarbons: hydrocarbon halides: nitrohydrocarbons; aliphatic-aromatic ethers; aromatic ethers; carboxylic acid esters; carboxylic acid nitriles; sulfones; phosphoric acid halides and phosphoric acid esters. Specific examples of suitable solvents are: trimethylpentane, decahydronaphthalene, toluene, 1,2-dichloroethane, chlorobenzene, chlorotoluene, 1,2-dichlorobenzene, nitrobenzene, anisole, phenetole, diphenylether, acetic acid butyl ester, tetramethylene sulfone, phosphoroxychloride and phosphoric acid trimethylester. Commercial chlorobenzene and commercial 1,2-dichlorobenzene are preferred solvents. Any mixtures of the above solvents may, of course, also be used. In most of the specific solvents listed above, the bis-(4-aminophenoxy)alkanes have slight or extremely limited solubility at low temperatures. Consequently, at low temperatures, the solvents named above act as suspending agents for the diamine or the hydrogen chloride or carbon dioxide adducts thereof. These solvents act as true solvents for the starting diamine and the product diisocyanate only at higher temperatures and as conversion of the starting diamine into the diisocyanate increases.

The mixture of starting material to be phosgenated and solvent used in the process of the present invention are generally "solution suspensions" containing a quantity of from about 2 to 70 wt % of diamine or diamine adduct. The term "solution suspension" is intended to mean that the starting materials (particularly the preferred diamines) are partially dissolved and partially suspended.

The phosgenation reaction according to the present invention may be carried out in a two-stage process according to the known principle of "cold-hot phosgenation" or in a one-stage process according to the principle of "hot phosgenation". In "cold-hot phosgenation", the starting material to be phosgenated is reacted at the beginning of the reaction, generally at a temperature of from $-20°$ to $+40°$ C. (preferably from $-10°$ to $+30°$ C.) and hot phosgenation is subsequently carried out at a temperature of from 40° to 260° C. (preferably from 80° to 220° C.). In this "cold-hot phosgenation" process, the range between the starting temperature and the elevated temperature can be transversed uniformly or in jumps.

In "hot phosgenation", the starting material to be phosgenated immediately contacts the phosgene at a temperature of from 40° to 260° C., preferably from 80° to 220° C.

So-called "cold-hot phosgenation" is the most preferred method of phosgenation for diamines (rather than the hydrogen chloride or carbon dioxide adduct). There is no appreciable reaction between the suspended diamine and the phosgene which is added at $-20°$ to 40° C. Only as the temperature subsequently rises and the solubility of the diamine increases does the diamine begin to react with the phosgene.

All phosgenation techniques of the present invention are preferably carried out under standard pressure or under elevated pressure. The reaction pressure is generally from 0.9 to 100, preferably from 1 to 60 bars.

The starting material to be phosgenated is generally brought together with from 1 to 10 times, preferably from 1.05 to 6 times, the stoichiometric quantity of phosgene in the phosgenation reaction. These quantities of phosgene may be introduced to the reaction mixture in one portion or in partial quantities. It may be advantageous, in a discontinuous process for example, to introduce part of the phosgene into the reaction mixture and to introduce the remaining parts into the reaction mixture in further portions or by dispensing phosgene continuously over a relatively long period.

Phosgenation of the diamines in accordance with the present invention may be accelerated, in principle, by addition of a catalyst (such as dimethylformamide) and/or acid acceptors (such as pyridine). However, the reaction rates for the phosgenation of the diamine are generally adequate without addition of such a catalyst.

The duration of the phosgenation reaction is dependent upon the reaction conditions used (particularly the reaction temperature), the excess of phosgene, the dilution with solvent and the catalysts and/or acid acceptors which may optionally be added.

On completion of the phosgenation reaction, the reaction mixture is worked up in known manner by separation of gaseous constituents (hydrogen chloride, excess phosgene) and removal of the solvent by distillation. If necessary, any solid by-products present may be removed by filtration or centrifugation before the solvent is removed by distillation. The crude product obtained as distillation residue after the removal of the solvent by distillation can, if required, be purified by recrystallization from a suitable inert solvent (such as toluene) or preferably by distillation. Thus, 1,2-bis-(4-isocyanatophenoxy) ethane for example, may be obtained as a colorless distillate under a pressure of from 3 to 5 mbars at a temperature of from 240° to 250° C. This distillate immediately hardens to produce a solid material having a melting point of from about 98° to 99° C.

Although the diisocyanates according to the present invention are heat-stable materials, it may be appropriate to purify the diisocyanates without substantial heat stressing (i.e. at moderate temperatures), using, for example, a thin layer evaporator. If desired, the diisocyanates of the present invention may be freed from troublesome by-products, such as heat-stable chlorine-containing compounds by tempering the diisocyanates at a temperature of from 160° to 250° C., pref. from 180° to 230° C. If the new diisocyanates of the present invention are used to produce isocyanate addition products such as polyurethane plastics (particularly bulk or cellular polyurethane elastomers), these diisocyanates are reacted with known isocyanate-reactive materials (see the aforementioned relevant literature and also "Kunststoff-Handbuch", Vol. VII, "Polyurethane" by Vieweg and Höchtlen, Carl Hanser Verlag Munich (1966), particularly pages 206 to 297).

More particularly, polyurethane elastomers may be produced from a diisocyanate of the present invention by reacting that diisocyanate with (a) a di- or trifunctional polyhydroxyl compound having a molecular weight of from 400 to 10,000, (preferably from 800 to 3000), preferably the corresponding polyhydroxy polyesters or polyhydroxy polyethers, (b) a chain lengthening agent having a molecular weight of from 60 to 399 (i.e., compounds with alcoholic hydroxyl groups or primary or secondary amino groups, which are difunctional in the context of the isocyanate addition reaction), optionally in the presence of (c) other auxiliaries and additives known to those skilled in polyurethane elastomer chemistry.

The isocyanate addition reaction can be carried out by the known prepolymer process by reacting the diisocyanate with the polyhydroxyl compound having a molecular weight of from 400 to 10,000 while maintaining an equivalent ratio of isocyanate groups to isocyanate group-reactive groups of more than 1.3:1 to form a prepolymer. The NCO prepolymers obtained in this manner are then reacted with a chain lengthening agent. The isocyanate addition reaction may also be carried out in a one-stage process by reacting the diisocyanate with a mixture of polyhydroxyl compound having a molecular weight of from 400 to 10,000 and chain lengthening agent. In both the prepolymer and one-stage processes, the equivalent ratio of isocyanate groups to the total quantity of isocyanate group-reactive groups is generally from 0.8:1 to 1.3:1, preferably from 0.95:1 to 1.1:1. The temperatures at which these reactions are carried out are generally from 60° to 180° C., preferably from 80° to 150° C. The reactions can take place in the presence or in the absence of suitable inert solvents.

The polyurethane plastics, particularly polyurethane elastomers produced from the diisocyanates of the present invention may be solid or cellular products. Both types of polyurethane elastomers are produced by known processes (described in e.g., "Kunststoff-Handbuch", Vol. VII, "Polyurethane" by Vieweg and Höchtlen, Carl Hanser Verlag Munich (1966), pages 206–297). For example, cellular polyurethane elastomers may be produced using water as a chain-lengthening agent.

The plastics produced with the diisocyanates of the present invention (particularly elastomers produced with the diisocyanates of the present invention in which the given hydrocarbon radical R is an ethylene, tetramethylene or hexamethylene group, preferably an ethylene or a tetramethylene group) have excellent mechanical and thermal properties. Consequently, they are extremely suitable for spring and damping elements, fenders, wheel coverings, seals, shoe soles and similar fields of use in which the material is subjected to extreme mechanical and thermal stresses.

The invention is further illustrated, but is not intended to be limited by the following examples in which all parts and percentages are by weight unless otherwise specified.

EXAMPLES

EXAMPLE 1

(Production of 1,2-bis-(4-isocyanatophenoxy)ethane)

366 g of crystalline 1,2-bis-(4-aminophenoxy)ethane (analytically-determined purity: 99.8%) were placed in a 6 l laboratory phosgenation apparatus and mixed with 4.4 l of water-free chlorobenzene. The resultant suspension was cooled in an ice bath. 320 g of phosgene were introduced without interruption into the suspension at a temperature of from 0° to 10° C. The mixture was then heated to reflux with stirring and slow introduction of phosgene (from 40 to 50 g/h) over a period of 2.5 hours. After an additional 1.5 hours of phosgenation (from 40 to 50 g of phosgene/h) at reflux, a clear solution was produced. The finished reaction mixture was freed from excess phosgene and from most of the solvent by distillation and then cooled to 50° C. Crystals precipitated. The remaining chlorobenzene was then completely distilled off from the pulpy suspension under vacuum at a temperature of 50° C. 446 g of crude product in the form of slightly brownish crystals with a melting point of from 96° to 97° C. were then obtained as residue. The crude product contained a quantity of 0.13% of hydrolyzable chlorine.

420 g of the crude diisocyanate obtained in this manner were subjected to vacuum distillation. 1,2-bis-(4-isocyanatophenoxy)-ethane distilled off under 1 mbar and at a temperature of from 210° to 225° C. (without first-runnings) as a colorless liquid which quickly hardened to produce crystals having a melting point of from 98° to 99° C.

| Yield: | 411 g (98.5% of the theoretical yield) | |
|---|---|---|
| $C_{16}H_{12}N_2O_4$ | (269.3) | |
| Hydrolyzable chlorine: | 170 ppm | |
| NCO content: | calculated: | 28.35% |
| | actual: | 28.2% |
| | | 28.3% |

When redistilled, the diisocyanate was virtually free from residue. The distillate contained a quantity of 50 ppm of hydrolyzable chlorine.

6 g of a dark-colored solid product with a melting point of from 350° to 360° C. (decomposition) remained as residue from the first distillation stage.

EXAMPLE 2

(Production of 1,2-bis-(4-isocyanatophenoxy)ethane)

Unpurified 1,2-bis-(4-aminophenoxy)-ethane was obtained by catalytic hydrogenation of 1,2-bis-(4-nitrophenoxy)-ethane. The diamine had an analytically determined purity of 95.4% by weight. 366 g of this diamine were placed in a 6 l laboratory phosgenation apparatus and mixed with 4.4 l of water-free o-dichlorobenzene. The suspension was cooled and 310 g of phosgene were added without interruption at a temperature of from 0° to 10° C. The mixture was then heated to reflux over a period of 3.5 hours with stirring and slow introduction of phosgene (from 40 to 50 g/h) and phosgenated at reflux for an additional hour. The finished dark colored reaction solution contained an insoluble flaky deposit. Excess phosgene and 2 l of dichlorobenzene were distilled off from the mixture. The deposit was drawn off by suction after cooling to room temperature, washed with dichlorobenzene and dried under vacuum. 19.7 g of a dark, amorphous solid product were obtained.

The clear reaction solution was distilled off under vacuum. After a first-running of dichlorobenzene, 410 g of 1,2-bis-(4-isocyanatophenoxy)-ethane (96.8% of the theoretical yield) distilled off as a slightly yellowish liquid which rapidly hardened.
Melting point: 95° to 97° C.
Hydrolyzable chlorine: 710 ppm
NCO content: 28.4%
Distillation residue: 8 g of a dark solid product The diisocyanate was redistilled and produced virtually colorless crystals with a melting point of from 98° to 99° C. and containing a quantity of 60 ppm of hydrolyzable chlorine.

EXAMPLE 3

(Production of 1,4-bis-(4-isocyanatophenoxy)-butane)

408 g of 1,4-bis-(4-aminophenoxy)-butane (analytically determined purity=99.9%) were reacted with phosgene in the same manner described in Example 1. 490 g of crude product in the form of brownish crystals with a melting point of from 95° to 97° C. were obtained. The crude product contained a quantity of 0.22% of hydrolyzable chlorine.

450 g of the crude diisocyanate obtained in this manner were subjected to vacuum distillation. 1,4-bis-(4-isocyanatophenoxy)-butane distilled off under 1 mbar and at a temperature of from 220° to 230° C. (without first-runnings) as a colorless liquid which rapidly hardened to produce crystals with a melting point of from 97° to 98° C.

| Yield: | 436 g (97.7% of the theoretical yield) | |
|---|---|---|
| $C_{18}H_{16}N_2O_4$ | (324.3) | |
| Hydrolyzable chlorine: | 190 ppm | |
| NCO content: | calculated: | 25.9% |
| | actual: | 26.0% |
| | | 25.9% |

When redistilled, the diisocyanate was virtually free from residue. The distillate contained a quantity of 70 ppm of hydrolyzable chlorine.

EXAMPLE 4

(Production of 1,6-bis-(4-isocyanatophenoxy)-hexane)

450 g of 1,6-bis-(4-aminophenoxy)-hexane (analytically determined purity: 96.1%) were reacted with phosgene by the same procedure described in Example 1. 519 g of crude product were obtained in the form of brownish crystals with a melting point of from 86° to 88° C. The crude product contained a quantity of 0.27% of hydrolyzable chlorine.

480 g of the crude diisocyanate obtained in this manner were subjected to vacuum distillation. 1,6-bis-(4-isocyanatophenoxy)-hexane distilled off under 0.3 mbars at a temperature of from 238° to 244° C. (without first-runnings) as a virtually colorless liquid which quickly hardened to crystals with a melting point of from 88° to 89° C.

| Yield: | 449 g (95.7% of the theoretical yield) |
|---|---|
| C$_{20}$H$_{20}$N$_2$O$_4$ | (352.4) |
| Hydrolyzable chlorine: | 140 ppm |
| NCO content: | calculated: 23.8% |
| | actual: 23.8% |
| | 23.7% |

When distilled, the diisocyanate was virtually free from residue. The distillate was colorless and contained a quantity of 60 ppm of hydrolyzable chlorine.

EXAMPLE 5

(a) (Production of 1,2-bis-(4-amino-3-methylphenoxy)ethane)

A mixture of 1989 g of 4-nitro-3-methylphenol, 2.5 l of ethylene glycol, 0.5 l of toluene and 1222 g of 1,2-dibromoethane was introduced into a distillation apparatus equipped with a water separator and azeotropically dehydrated under reflux (approx. 130° C.) with stirring. 1040 g of 50% aqueous sodium hydroxide were then added to the mixture boiling under reflux over a period of 2 hours with separation of water. After the addition of another 244 g of 1,2-dibromoethane and 104 g of 50% aqueous sodium hydroxide solution, the reaction mixture was stirred for another 4.5 hours at 130° C. and then cooled to room temperature, followed by the addition of 3 l of water with vigorous stirring. The crystals precipitated were filtered off, washed with water and methanol and dried. 1880 g (87% of the theoretical yield) of 1,2-bis-(4-nitro-3-methylphenoxy)-ethane in the form of sand-colored crystals melting at 182° C. and having the following analysis:

| C$_{18}$H$_{16}$N$_2$O$_6$ | (332.3) | | | |
|---|---|---|---|---|
| Calculated: | C 57.83% | H 4.85% | N 8.43% | O 28.89% |
| Observed: | 57.8% | 4.8% | 8.4% | 28.6% | were obtained.

A solution of 1695 g of the dinitro compound in 5 l of dimethyl formamide was then introduced into a hydrogenation autoclave and, after the addition of Raney nickel, was reacted while stirring by introducing hydrogen under pressure. Hydrogenation was carried out for 2 hours at 75° C./40–50 bar and then for 1 hour at 90° C./40–50 bar. After venting of the autoclave, the hot reaction mixture was removed, freed from the catalyst by filtration and cooled to room temperature. The crystals which precipitated were filtered off under suction and dried in vacuo. The mother liquor was concentrated by evaporation in vacuo (more product being left behind). A total of 1365 g of 1,2-bis-(4-amino-3-methylphenoxy)-ethane was obtained in the form of brownish crystals. Titration with perchloric acid in glacial acetic acid showed the product to be 98.6% pure (yield: 97% of the theoretical, based on the dinitro compound used). Substantially colorless crystals melting at 106° to 107° C. were obtained by purifying the diamine by distillation

| (boiling point: | 195 to 200° C. at 0.2 mbar). |
|---|---|
| C$_{16}$H$_{20}$N$_2$O$_2$ | (272.3) |

(b) (Production of 1,2-bis-(4-isocyanato-3-methylphenoxy)-ethane)

A solution of 350 g of phosgene in 3.8 l of anhydrous chlorobenzene was introduced into a 6-liter laboratory phosgenation apparatus, after which 408 g of 1,2-bis-(4-amino-3-methylphenoxy)-ethane (analytically determined purity: 98.6%) were added with cooling at 0° to 10° C. The reaction mixture was then heated to reflux temperature over a period of 2 hours during which more phosgene was introduced. After another 2 hours' phosgenation under reflux, a clear solution had formed. The reaction mixture was then freed from excess phosgene and from the solvent by distillation. The crude product remaining behind was purified by distillation in vacuo. 1,2-bis-(4-isocyanato-3-methylphenoxy)-ethane distilled over without first runnings at 206°–218° C./0.5 mbar in the form of an almost colorless liquid which rapidly hardened into crystals melting at 111°–113° C.

| Yield: | 464 g (96.8% of the theoretical) |
|---|---|
| NCO-content: | calculated 25.9% |
| | observed 25.7%/25.9% |
| Distillation residue: | 19 g of dark-colored resin hardening like glass |

The diisocyanate could be almost completely redistilled and gave colorless crystals melting at 113°–114° C. and containing 20 ppm of hydrolyzable chlorine.

EXAMPLE 6

(Production of 1,4-bis-(4-isocyanato-3-methylphenoxy)-butane)

450 g of 1,4-bis-(4-amino-3-methylphenoxy)-butane (analytically determined purity: 98.2%) were reacted with phosgene as in Example 5b). The crude product obtained was purified by vacuum distillation. 1,4-bis-(4-isocyanato-3-methylphenoxy)-butane distilled over without first runnings at 205°–210° C./0.2 mbar in the form of a colorless liquid which hardened into crystals melting at 89° to 91° C.

| Yield: | 503 g (97.0% of the theoretical) |
|---|---|
| C$_{20}$H$_{20}$N$_2$O$_4$ | (352.4) |
| NCO-content: | calculated 23.8% |
| | observed 23.9%/23.8% |
| Distillation residue: | 21 g of dark-colored product |

The diisocyanate could be almost completely redistilled and gave colorless crystals melting at 90° to 91° C. and containing 32 ppm of hydrolyzable chlorine.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A bis-(4-isocyanatophenoxy)-alkane corresponding to the formula

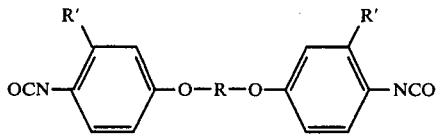

in which

R represents a divalent, saturated aliphatic hydrocarbon radical having from 2 to 6 carbon atoms with at least two carbon atoms between the two ether oxygen atoms and R' represents hydrogen or a methyl group with R' being the same on both rings.

2. The bis-(4-isocyanatophenoxy)-alkane of claim 1 in which R represents an ethylene, tetramethylene or hexamethylene radical.

3. The bis-(4-isocyanatophenoxy)-alkane of claim 2 in which R' represents hydrogen.

4. The bis-(4-isocyanatophenoxy)-alkane of claim 2 in which R' represents a methyl group.

5. The bis-(4-isocyanatophenoxy)-alkane of claim 1 in which R' represents hydrogen.

6. The bis-(4-isocyanatophenoxy)-alkane of claim 1 in which R' represents a methyl group.

7. The bis-(4-isocyanatophenoxy)-alkane of claim 1 in which R represents an ethylene radical and R' represents hydrogen.

8. The bis-(4-isocyanatophenoxy)-alkane of claim 1 in which R represents an ethylene radical and R' represents a methyl group.

* * * * *